United States Patent
Bellini et al.

(10) Patent No.: US 12,252,455 B2
(45) Date of Patent: Mar. 18, 2025

(54) PROCESS FOR THE CONTINUOUS PREPARATION OF HEAVY ALKYL ACRYLATES

(71) Applicant: ARKEMA FRANCE, Colombes (FR)

(72) Inventors: Clement Bellini, Saint Avold (FR); Sandra Maget, Saint Avold (FR); Patrice Defer, Saint Avold (FR)

(73) Assignee: Arkema France, Colombes (FR)

( * ) Notice: Subject to any disclaimer, the term of this patent is extended or adjusted under 35 U.S.C. 154(b) by 534 days.

(21) Appl. No.: 17/781,394

(22) PCT Filed: Dec. 9, 2020

(86) PCT No.: PCT/FR2020/052365
§ 371 (c)(1),
(2) Date: Jun. 1, 2022

(87) PCT Pub. No.: WO2021/116608
PCT Pub. Date: Jun. 17, 2021

(65) Prior Publication Data
US 2023/0002310 A1  Jan. 5, 2023

(30) Foreign Application Priority Data
Dec. 9, 2019 (FR) ...................................... 1913924

(51) Int. Cl.
*C07C 213/06* (2006.01)

(52) U.S. Cl.
CPC .................................. *C07C 213/06* (2013.01)

(58) Field of Classification Search
CPC ............................ C07C 213/06; C07C 219/20
See application file for complete search history.

(56) References Cited

U.S. PATENT DOCUMENTS

| 3,872,161 A * | 3/1975 | Fukuchi ................. C07C 69/54 |
| | | 560/217 |
| 5,242,877 A | 9/1993 | Dobson et al. |
| 6,437,173 B1 | 8/2002 | Hurtel et al. |
| 2008/0161596 A1 | 7/2008 | Riondel et al. |
| 2013/0178592 A1 | 7/2013 | Bette et al. |
| 2019/0071384 A1 | 3/2019 | Elmaloglou et al. |

FOREIGN PATENT DOCUMENTS

| CA | 2811363 A1 | 3/2012 |
| JP | 2001172234 A2 | 6/2001 |
| JP | 2001187763 A2 | 7/2001 |
| WO | WO08125787 A1 | 10/2008 |

* cited by examiner

*Primary Examiner* — Deborah D Carr
(74) *Attorney, Agent, or Firm* — Debodhonyaa Sengupta

(57) ABSTRACT

The present invention relates to a process for the continuous synthesis of heavy alkyl acrylates by a transesterification reaction using hydrozincite as a heterogeneous catalyst.

13 Claims, No Drawings

PROCESS FOR THE CONTINUOUS PREPARATION OF HEAVY ALKYL ACRYLATES

CROSS-REFERENCE TO RELATED APPLICATIONS

This application is a national stage application under 35 U.S.C. § 371 of PCT/FR2020/052365, filed Dec. 9, 2020 which claims benefit to application FR19.13924, filed Dec. 9, 2019.

FIELD OF THE INVENTION

The present invention relates to a process for the continuous synthesis of heavy alkyl acrylates by transesterification reaction, using a heterogeneous catalyst.

TECHNICAL BACKGROUND

Transesterification is a process commonly used for producing (meth)acrylic esters. It is known practice to prepare the (meth)acrylic esters of formula (I):

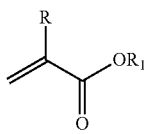
(I)

in which R is a hydrogen atom or a methyl group, and $R_1$ may be a linear or branched alkyl radical, or a cycloaliphatic, aryl, alkylaryl or arylalkyl radical, which may contain heteroatoms, via a transesterification process by reaction of an alkyl (meth)acrylate of formula (II):

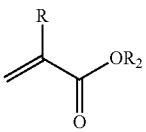
(II)

in which R has the abovementioned meaning and $R_2$ may be a linear or branched alkyl group containing from 1 to 4 carbon atoms,
with an alcohol of formula (III):

$R_1$—OH    (III)

in which $R_1$ has the abovementioned meaning.

Light alcohol $R_2$—OH is generated in the course of the synthesis, and is removed in the form of an azeotrope with the light alkyl (meth)acrylate (II).

The synthesis of (meth)acrylic esters by transesterification generally takes place in the presence of a catalyst, which may be homogeneous or heterogeneous. The choice of the catalyst depends on various criteria, notably on the nature of the alkyl (meth)acrylate (II) or of the alcohol (III) used, but also on the nature of the process, such as a batch process or a continuous process.

For example, the alkoxy titanates described in FR 2777561 and FR 2876375 or the tin oxide derivatives described in JP 2001172234 and JP 2001187763 enable very selective catalysis of the formation of acrylic esters by transesterification. In all cases, a preliminary step of purification for removal of the catalyst by tailing is necessary, since said catalyst is a poison for the purification of heavy alkyl acrylates by distillation.

In order to reduce the costs of using the catalyst and to facilitate its recycling into the reaction, supported heterogeneous catalysts were developed for the synthesis of heavy alkyl acrylates by transesterification reaction. Catalysts on metallic polymer supports, of titanium (FR 2913612) or of zirconium (EP 0557131) are used in one or more transesterification reactors in series. However, these catalysts have relatively short service lives, due to the high temperatures associated with the transesterification reaction.

The use of inorganic salts that are insoluble in the reaction medium as transesterification catalyst for the production of aminoalkyl (meth)acrylates was described in US 2013/178 592. The addition of water to the reaction (300-3000 ppm) makes it possible notably to improve the selectivity of these heterogeneous catalysts. However, $K_3PO_4$, which is the catalyst preferentially chosen, is very sparingly selective (<25%) in the synthesis of acrylic esters.

FR 2175104 describes a process for the synthesis of aminoalkyl acrylates in the presence of a zinc compound, the molar content of which is between 0.01% and 30% relative to the alkylamino alcohol. Among the numerous catalysts consisting of zinc compounds listed in said document is basic zinc carbonate, described in example 28. More particularly, said example describes the synthesis of dimethylaminoethyl acrylate by means of a transesterification process performed in batch mode, starting with ethyl acrylate and dimethylaminoethanol, in the presence of phenothiazine and basic zinc carbonate, the content of said carbonate being 1.045 mol % relative to the dimethylaminoethanol. It reports a yield of 84.5% of dimethylaminoethyl acrylate. However, the corresponding catalytic activity, determined relative to the TOF (turnover frequency) value, calculated according to the formula indicated below, is very low (only 9.5 $h^{-1}$).

Consequently, there is at the present time a need for a transesterification process that is suitable for the continuous manufacture of heavy alkyl acrylates, which overcomes the drawbacks listed above.

To this end, the invention provides a process for the continuous synthesis of heavy alkyl acrylates by transesterification reaction using hydrozincite (of formula $Zn_5(CO_3)_2(OH)_6$ or $[ZnCO_3]_2 \cdot [Zn(OH)_2]_3$ or $C_2H_{12}O_{12}Zn_5$) as heterogeneous catalyst. This catalyst makes it possible to obtain very high production yields when it is employed in very low contents (molar content of less than 1% relative to the heavy alcohol), while at the same time maintaining high catalytic activity.

Furthermore, since the catalyst is separated from the reaction mixture by filtration, purification of the desired alkyl acrylate takes place in only two steps (topping and then tailing), by means of two distillation columns, instead of three steps, as reported in the prior art.

SUMMARY OF THE INVENTION

The invention relates to a process for the continuous synthesis of (meth)acrylic esters of formula (I):

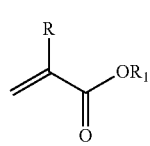
(I)

in which R is a hydrogen atom or a methyl group, and $R_1$ is a linear or branched alkyl radical, or a cycloaliphatic, aryl, alkylaryl or arylalkyl radical, including from 4 to 40 carbon atoms, or a linear or branched alkyl radical containing at least one heteroatom and from 3 to 40 carbon atoms, by reaction of an alkyl (meth)acrylate of formula (II):

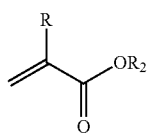
(II)

in which R has the abovementioned meaning and $R_2$ is a linear or branched alkyl group containing from 1 to 3 carbon atoms,
with an alcohol of formula (III):

(III)

in which $R_1$ has the abovementioned meaning, in the presence of hydrozincite as heterogeneous catalyst.

Characteristically, the process uses a catalyst content ranging from 0.01 mol % to 0.5 mol % relative to the alcohol.

Advantageously, the purification of the alkyl acrylate takes place in two steps: topping and then tailing, by means of two distillation columns.

The present invention makes it possible to overcome the drawbacks of the prior art. The invention more particularly provides a simplified, economic and efficient synthetic method for the continuous manufacture of heavy alkyl acrylates. The invention notably makes it possible to greatly reduce the costs of using the catalyst, to improve the production yields and to avoid the treatment of metal residues at the plant outlet.

Furthermore, this method, which requires very low contents of catalysts, has very high yields of final product. The catalytic efficiency, quantified by means of the TOF, is greatly improved, and is up to values of greater than 50 $h^{-1}$.

DESCRIPTION OF EMBODIMENTS OF THE INVENTION

The invention is now described in greater detail and in a nonlimiting manner in the description that follows.

The synthesis of heavy alkyl acrylates by transesterification reaction by homogeneous catalysis involves a preliminary step of removing the catalyst by distillation (tailing). A portion of the tail from this distillation containing the metal residue is sent for destruction (outside recycling), markedly increasing the costs of using the catalyst and the associated ecological impact.

Moreover, the head from this distillation contains the desired heavy alkyl acrylate, and also the light alkyl acrylate and the unreacted heavy alcohol. An additional distillation (heading) is required in order to separate the heavy alkyl acrylate from the lighter starting materials. The tail from this second distillation then contains the desired heavy alkyl acrylate and the excess polymerization inhibitor(s). A final distillation step (purification) is then required in order to obtain the desired heavy alkyl acrylate in the desired specifications.

Removal of the catalyst directly in the reaction would thus enable this purification process to be performed in only two steps (heading and then tailing) instead of three, lowering the construction cost of a production plant, and also the costs associated with the energy required for the production.

The present invention relates to a process for the continuous synthesis of heavy alkyl acrylates by transesterification reaction using hydrozincite as heterogeneous catalyst, the purification of the final product being performed in two steps.

The invention relates to a process for the continuous synthesis of (meth)acrylic esters of formula (I):

(I)

in which R is a hydrogen atom or a methyl group, and $R_1$ is a linear or branched alkyl radical, or a cycloaliphatic, aryl, alkylaryl or arylalkyl radical, including from 4 to 40 carbon atoms, or a linear or branched alkyl radical containing at least one heteroatom and from 3 to 40 carbon atoms, by reaction of an alkyl (meth)acrylate of formula (II):

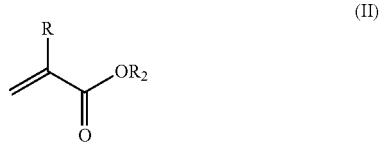
(II)

in which R has the abovementioned meaning and $R_2$ is a linear or branched alkyl group containing from 1 to 3 carbon atoms, with an alcohol of formula (III):

(III)

in the presence of at least one polymerization inhibitor and of hydrozincite as heterogeneous catalyst, characterized in that the catalyst content is between 0.01 mol % and 0.5 mol % relative to the alcohol.

According to various embodiments, said process comprises the following features, combined where appropriate.

According to one embodiment, the transesterification reaction takes place in a reactor stirred at a temperature of 80-150° C., preferably between 90 and 130° C., the reaction mixture exiting the reactor comprising the heavy alkyl acrylate with, as light products, the heavy alcohol, the light alcohol and the unreacted light acrylate, and, as heavy products, the polymerization inhibitor(s) and also heavy reaction products. The light acrylate/light alcohol azeotropic mixture is removed by means of a distillation column (azeotropic column) mounted on the reactor. The reaction mixture is subjected to a liquid/solid separation step to separate out the catalyst.

The catalyst may be introduced into the reaction as a suspension in the reaction mixture or else placed in a fixed bed in the transesterification reactor(s). The usual liquid/solid separation techniques (filtration, electrofiltration, absorption, centrifugation or decantation) allow extraction at the reactor outlet of a crude product that is free or substantially free of catalyst (catalyst content of less than 500 ppm).

According to one embodiment, the polymerization inhibitor comprises at least one N-oxyl compound and at least one polymerization inhibitor other than an N-oxyl compound.

The N-oxyl compound is chosen from 2,2,6,6-tetramethylpiperidine 1-oxyl (called TEMPO), and derivatives thereof such as 4-hydroxy-2,2,6,6-tetramethylpiperidine 1-oxyl (4-OH-TEMPO or 4-HT), or 4-oxo-2,2,6,6-tetramethylpiperidine 1-oxyl (4-Oxo-TEMPO), and also a mixture of these compounds.

According to one embodiment, the polymerization inhibitor is chosen from phenol compounds and phenothiazine compounds.

The term "phenol compound" means compounds derived from phenol, from naphthol, and quinones. As phenol compounds, mention may be made of the following compounds, without this list being limiting: p-aminophenol, p-nitrosophenol, 2-tert-butylphenol, 4-tert-butylphenol, 2,4-di-tert-butylphenol, 2-methyl-4-tert-butylphenol, 4-methyl-2,6-tert-butylphenol (or 2,6-tert-butyl-p-cresol) or 4-tert-butyl-2,6-dimethylphenol, hydroquinone (HQ), hydroquinone methyl ether (HQME).

The term "phenothiazine compound" means phenothiazine and derivatives thereof, preferably phenothiazine (PTZ). Preferably, the stabilizing composition comprises at least one polymerization inhibitor chosen from phenothiazine, 4-methyl-2,6-tert-butylphenol, hydroquinone and hydroquinone methyl ether.

According to one embodiment, the N-oxyl compound is in excess in the stabilizing composition.

According to one embodiment, the mass ratio of the N-oxyl compound to the polymerization inhibitor(s) is between 1 and 10, preferably between 2 and 10, more preferentially between 4 and 10, in particular between 5 and 10, the mass ratio being expressed with the limits included.

Advantageously, the total mass content of polymerization inhibitor is from 0.001% to 0.5% in the reaction mixture.

Advantageously, the (meth)acrylic ester of formula (I) is purified according to the steps below:
  a. said reaction mixture is sent to a first distillation column (C1) under reduced pressure (from 1000 to 20 000 Pa) and a distillation is performed therein, producing:
    at the top, a stream comprising unreacted starting materials, and a minor fraction of heavy products (the Michael adducts), and
    at the tail, a stream composed essentially of the heavy alkyl acrylate;
  b. the tail stream from the first distillation column (C1) is sent to a second distillation column (C2) under reduced pressure (from 1000 to 20 000 Pa), in which a distillation is performed producing:
    at the top, the desired heavy alkyl acrylate,
    at the tail, the polymerization inhibitor, and also heavy reaction products.

According to one embodiment, the process according to the invention comprises an additional step in which the head stream from the first distillation column (C1) is sent to the transesterification reactor in order to recycle the starting materials.

According to one embodiment, in the reactor, the mole ratio between the alkyl (meth)acrylate of formula (II) (known as the "heavy alkyl acrylate") and the alcohol of formula (III) (known as the "heavy alcohol") is between 1.1 and 3, preferably between 1.7 and 2.2.

According to one embodiment, the (meth)acrylic ester of formula (I) is dimethylaminoethyl acrylate.

According to one embodiment, the alcohol is dimethylaminoethanol.

It has been found, surprisingly, that the process according to the invention makes it possible to greatly reduce the formation of Michael adducts, which result from Michael addition reactions of an alcohol molecule (containing a labile hydrogen atom) on the double bond of the (meth)acrylic ester, during the transesterification reaction of (meth)acrylic derivatives. This is notably observed relative to the formation of Michael adducts in the presence of high concentrations of basic zinc carbonate catalyst.

For example, in the case of the production of DMAEA by transesterification between a light acrylate, such as methyl acrylate (MA) or ethyl acrylate (EA), and N,N-dimethylaminoethanol (DMAE), the as yet unreacted alcohol or the light alcohols generated during the reaction (methanol or ethanol) are added at the double bond of the already formed DMAEA or of the unreacted light acrylate (MA or EA), to form heavy Michael addition by-products [DMAE+DMAEA].

These heavy by-products are generally concentrated in a "heavy fraction" separated out during the process for the purification of the crude DMAEA. The removal of this heavy fraction generally poses a problem since it must be incinerated, and leads to significant losses of starting materials (notably DMAE) and of finished product (DMAEA) which are present in this fraction in free form or in the form of Michael adducts.

Now, the measures for the concentration as adducts of this type in the tail stream from the first distillation column (C1) of the process according to the invention show that their mass content does not exceed 5%, this value being significantly lower than those measured in the heavy fractions obtained via the process described in FR 2175104, and when the catalyst content is greater than 0.5 mol % relative to the alcohol.

The content of Michael adducts is measured by gas chromatography. Moreover, it has been found that the process according to the invention using hydrozincite as heterogeneous catalyst in very low contents (molar content ranging from 0.01% to 0.5%, limits inclusive, relative to the heavy alcohol), makes it possible to obtain very high production yields, this being accompanied by high catalytic activity. More precisely, the catalytic activity is determined by the TOF (turnover frequency) value, calculated according to the formula below. The residence time is determined as a function of the extraction flow rate at the bottom of the transesterification reactor.

$$TOF = \frac{N_{DMAEA}}{N_{Catalyst} \times TdS}$$

The process according to the invention is characterized by TOF values of greater than 50 h$^{-1}$.

EXAMPLES

The examples that follow illustrate the invention without limiting it.

General Protocol for Examples 1 to 3

In the examples that follow, the following abbreviations were used:
EA: Ethyl acrylate
DMAE: Dimethylaminoethanol
DMAEA: Dimethylaminoethyl acrylate PTZ: Phenothiazine
4-HT: 4-OH-TEMPO
$Zn_5(CO_3)_2(OH)_6$: Hydrozincite
$Ti(OEt)_4$: Tetraethyl titanate
TOF: Turnover frequency (catalytic efficiency or activity)

The EA, the heavy alcohol (DMAE), and a transesterification catalyst ($Ti(OEt)_4$) or $Zn_5(CO_3)_2(OH)_6$) are introduced continuously into a stirred 0.5 L reactor, heated by circulation of oil thermostatically maintained at 135° C. in a jacket, and on which reactor is mounted a distillation column with Multiknit packing, with a condenser containing water-glycol mixture at the column head, a reflux head, a vacuum separator, receivers and traps. The polymerization inhibitors (PTZ, 4-HT, HQME or a mixture of these compounds) are injected continuously at the top as a mixture with the EA.

Throughout the synthesis, air is sparged into the reaction mixture. The reaction is performed at a temperature of 119-121° C. under a vacuum of 86 to 87 kPa (860 to 870 mbar). The ethanol formed during the reaction is removed gradually as it is formed, as an EA/ethanol azeotrope. The degree of conversion is monitored by refractometric analysis of the azeotrope. The ethanol content is between 58% and 62%. The crude reaction mixture is extracted by means of an overspill and recovered in a receiver.

The content of heavy alcohol, heavy (meth)acrylate (DMAEA) and ethanol in the distillate and tail streams is analyzed, after 120 hours of running, by gas chromatography in order to determine the yield of desired ester, the conversion of the heavy alcohol and the selectivity. The inhibitors are analyzed and quantified by the HPLC method. The heavy impurities (catalyst+polymer) are quantified using a thermal balance. All the concentrations are given as mass percentages and ppm by mass, unless otherwise mentioned.

On the basis of these analyses, the catalytic activity after 120 h is also determined by the TOF value, calculated by means of the formula indicated above.

Example 1—Continuous Synthesis of DMAEA with 0.2 Mol % Hydrozincite (According to the Invention)

The catalyst is introduced into the feed tank and stirred mechanically. The reaction mixture containing the EA (61.7 g/h), the DMAE (34.2 g/h) and the catalyst (0.4 g/h) are then introduced continuously into the reactor.

The temperature in the reactor is maintained at 120° C. for 120 hours and the reaction mixture is recovered by overspill (78.4 g/h) into a storage tank. At the end of the 120 hours, the reaction mixture and the azeotropic mixture are analyzed, thus giving the following results:
yield of DMAEA=82.0%
DMAE conversion=80.8%
Sum of the adducts=4.5%
TOF=71.6 $h^{-1}$.

Example 2—Continuous Synthesis of DMAEA with 0.8 Mol % Hydrozincite (Comparative)

The catalyst is introduced into the feed tank as a suspension and stirred mechanically. The reaction mixture containing the EA (64.3 g/h), the DMAE (35.7 g/h) and the catalyst (1.7 g/h) are then introduced continuously into the reactor.

The temperature in the reactor is maintained at 120° C. for 120 hours and the reaction mixture is recovered by overspill (78.5 g/h) into a storage tank. At the end of the 120 hours, the reaction mixture and the azeotropic mixture are analyzed, thus giving the following results:
yield of DMAEA=83.4%
DMAE conversion=83.7%
Sum of the adducts=7.7%
TOF=18.3 $h^{-1}$.

Example 3—Continuous Synthesis of DMAEA with 0.2 Mol % Ti(OEt) (Comparative)

The catalyst $Ti(OEt)_4$ is introduced homogeneously into the feed tank. The reaction mixture containing the EA (64.2 g/h), the DMAE (35.6 g/h) and the catalyst (0.2 g/h) are then introduced continuously into the reactor.

The temperature in the reactor is maintained at 120° C. for 120 hours and the reaction mixture is recovered by overspill (82.5 g/h) into a storage tank. At the end of the 120 hours, the reaction mixture and the azeotropic mixture are analyzed, thus giving the following results:
yield of DMAEA=53.6%
DMAE conversion=55.5%
Sum of the adducts=0.7%
TOF=45.5 $h^{-1}$.

The catalytic activity is higher (higher TOF values) when the hydrozincite concentration is lowered to 0.2 mol % relative to the DMAE (example 1), which is not the case for the ethyl titanate (example 3), due to the loss of yield.

Furthermore, the formation of Michael adducts is lower when the hydrozincite concentration is lowered to 0.2 mol % relative to the DMAE (example 1) in comparison with a higher concentration (comparative example 2). This correspondence between catalyst concentration and formation of Michael adducts is not observed with ethyl titanate (comparative example 3).

Examples 4 and 5

Example 4—Purification of the Crude Reaction $Zn_5(CO_3)_2(OH)_6$ after Filtration (According to the Invention)

A sample of the crude reaction mixture (0.5 L) obtained after 120 hours in example 2 is filtered to remove the catalyst in suspension. The filtrate is then placed in a stirred 0.5 L reactor, heated by circulation of oil thermostatically maintained at 100° C. in a jacket, and on which reactor is mounted a distillation column with Multiknit packing, with a condenser containing water-glycol mixture at the column head, a reflux head, a vacuum separator, receivers and traps.

The reaction mixture is then distilled under a rigorous vacuum (32 to 15 kPa) in order to extract a first column head fraction predominantly composed of EA. The same operation is performed under a more rigorous vacuum (15 to 4 kPa) in order to extract a second column head fraction predominantly composed of DMAE.

Finally, the DMAEA is purified by distillation by applying a vacuum of 12 kPa while raising the oil temperature to 140° C. The purified acrylate is collected in a column head receiver. GC analysis gives the following composition:
DMAEA purity=99.9%
Residual EA=243 ppm
Residual DMAE=557 ppm.

The purity of the DMAEA is acceptable (>99.8%) and the content of the light products EA/DMAE derived from the decomposition of the DMAEA by the action of the catalyst is below the specifications desired for this product (300 ppm for EA and 1000 ppm for DMAE).

Example 5—Purification of the Crude Reaction Ti(OEt)$_4$ (Counter Example)

A sample of the crude reaction mixture (0.5 L) obtained after 120 hours in example 3 is placed in a stirred 0.5 L reactor, heated by circulation of oil thermostatically maintained at 100° C. in a jacket, and on which reactor is mounted a distillation column with Multiknit packing, with a condenser containing water-glycol mixture at the column head, a reflux head, a vacuum separator, receivers and traps.

The filtration step is not performed since the Ti(OEt)$_4$ catalyst is soluble without heating.

GC analysis of the DMAEA gives the following composition:

DMAEA purity=99.7%
Residual EA=1602 ppm
Residual DMAE=1016 ppm

The purity of the DMAEA is unacceptable (<99.8%) and the content of the light products EA/DMAE derived from the decomposition of the DMAEA by the action of the catalyst is above the specifications desired for this product (300 ppm for EA and 1000 ppm for DMAE).

The invention claimed is:

1. A process for the continuous synthesis of (meth)acrylic esters of formula (I):

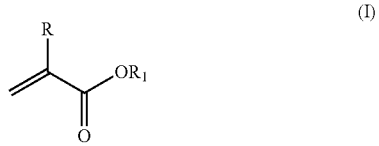
(I)

in which R is a hydrogen atom or a methyl group, and R$_1$ is a linear or branched alkyl radical, or a cycloaliphatic, aryl, alkylaryl or arylalkyl radical, including from 4 to 40 carbon atoms, or a linear or branched alkyl radical containing at least one heteroatom and from 3 to 40 carbon atoms, comprising the step of reacting an alkyl (meth)acrylate of formula (II):

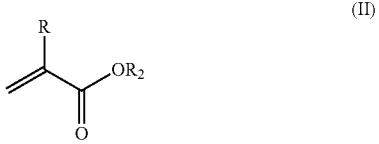
(II)

in which R has the abovementioned meaning and R$_2$ is a linear or branched alkyl group containing from 1 to 3 carbon atoms, with an alcohol of formula (III):

in the presence of at least one polymerization inhibitor and hydrozincite as heterogeneous catalyst,
wherein the catalyst content is between 0.01 mol_% and 0.5 mol % relative to the alcohol.

2. The process as claimed in claim 1 which is a transesterification reaction taking place in a transesterification reactor stirred at a temperature of 80-150° C., a reaction mixture exiting the reactor comprising the heavy alkyl acrylate with, as light products, heavy alcohol, light alcohol and unreacted light acrylate, and, as heavy products, the polymerization inhibitor(s) and heavy reaction products,
further comprising the step of subjecting said reaction mixture to a liquid/solid separation step to separate out the catalyst.

3. The process as claimed in claim 2, in which said (meth)acrylic ester of formula (I) is purified according to the steps below:
a. sending said reaction mixture to a first distillation column (C1) having a top and tail and under a pressure of 1000 to 20,000 Pa, and performing a first distillation therein, producing:
at the top, a head stream comprising unreacted starting materials, and a minor fraction of heavy products (Michael adducts), and
at the tail, a stream composed essentially of the heavy alkyl acrylate;
b. sending the tail stream from the first distillation column (C1) to a second distillation column (C2) having a top and a tail and under a pressure of 1000 to 20,000 Pa, and performing a second distillation producing:
at the top, the desired heavy alkyl acrylate,
at the tail, the polymerization inhibitor, and also heavy reaction products.

4. The process as claimed in claim 3, comprising an additional step of sending the head stream from the first distillation column (C1) to the transesterification reactor in order to recycle the starting materials.

5. The process as claimed in claim 2, in which said liquid/solid separation step involves a technique selected from the group consisting of: filtration, electrofiltration, absorption, centrifugation and decantation, the catalyst content of product thus treated being less than 500 ppm.

6. The process as claimed in claim 2 in which said catalyst is introduced into the transesterification reaction as a suspension in the reaction mixture or is placed in a fixed bed in the transesterification reactor.

7. The process as claimed in claim 1 in which said polymerization inhibitor comprises at least one N-oxyl derivative and at least one polymerization inhibitor chosen from phenol compounds and phenothiazine compounds in a mass ratio of between 1 and 10, limits included.

8. The process as claimed in claim 7, in which the N-oxyl compound is chosen from 2,2,6,6-tetramethylpiperidine 1-oxyl (TEMPO), and derivatives thereof, 4-hydroxy-2,2,6,6-tetramethylpiperidine 1-oxyl (4-OH-TEMPO), 4-oxo-2,2,6,6-tetramethylpiperidine 1-oxyl (4-Oxo-TEMPO), and mixture(s) thereof.

9. The process as claimed in claim 1 in which said polymerization inhibitor is chosen from phenol compounds and phenothiazine compounds.

10. The process as claimed in claim 1 in which the polymerization inhibitor is chosen from the group consisting of phenothiazine, 4-methyl-2,6-tert-butylphenol, hydroquinone, hydroquinone methyl ether, p-aminophenol, p-nitrosophenol, 2-tert-butylphenol, 4-tert-butylphenol, 2,4-di-tert-butylphenol, 2-methyl-4-tert-butylphenol, 4-methyl-2,6-tert-butylphenol (or 2,6-tert-butyl-p-cresol) or 4-tert-butyl-2,6-dimethylphenol, hydroquinone (HQ), and hydroquinone methyl ether (HQME).

11. The process as claimed in claim 1 in which a mass content of polymerization inhibitor is from 0.001% to 0.5% in the reaction mixture.

12. The process as claimed in claim 1 in which a mass content of Michael adducts in the tail stream from the first distillation column (C1) is less than or equal to 5%.

13. The process as claimed in claim 1 in which the (meth)acrylic ester of formula (I) is dimethylaminoethyl acrylate.

* * * * *